United States Patent
Reason et al.

(10) Patent No.: US 6,193,872 B1
(45) Date of Patent: Feb. 27, 2001

(54) PROCESS AND PLANT FOR TREATING AN AQUEOUS WASTE STREAM CONTAINING AT LEAST ONE ALKALI METAL CARBOXYLATE

(75) Inventors: Arthur James Reason, Saltburn; George Edwin Harrison, Billericay; Richard Clive Spratt, Harrow, all of (GB)

(73) Assignee: Kvaerner Process Technology Limited, London (GB)

(*) Notice: Subject to any disclaimer, the term of this patent is extended or adjusted under 35 U.S.C. 154(b) by 0 days.

(21) Appl. No.: 09/297,228
(22) PCT Filed: Oct. 23, 1997
(86) PCT No.: PCT/GB97/02922
 § 371 Date: Jun. 22, 1999
 § 102(e) Date: Jun. 22, 1999
(87) PCT Pub. No.: WO98/18726
 PCT Pub. Date: May 7, 1998

(30) Foreign Application Priority Data

Oct. 25, 1996 (EP) .................................................. 96307749

(51) Int. Cl.$^7$ ..................................................... C25B 1/16
(52) U.S. Cl. ......................... 205/510; 205/549; 205/554; 205/512; 204/263
(58) Field of Search ................... 205/510, 549, 205/554, 512; 204/252, 263

(56) References Cited

U.S. PATENT DOCUMENTS

| 3,134,729 | 5/1964 | Kerti ........................ 204/99 |
| 4,041,129 | 8/1977 | Foster et al. .................. 423/234 |
| 4,504,373 | 3/1985 | Mani et al. .................... 204/180 |
| 4,561,945 | 12/1985 | Coker et al. .................... 204/98 |
| 4,752,363 | 6/1988 | Buckley et al. ................... 204/98 |
| 5,098,532 | 3/1992 | Thompson et al. ................. 204/98 |

FOREIGN PATENT DOCUMENTS

| 0 531 999 A1 | 3/1993 | (EP) | ............................. B01D/61/44 |
| 0 532 188 A2 | 3/1993 | (EP) | ............................. C25B/1/16 |
| 0 631 988 A1 | 1/1995 | (EP) | ............................. C02F/1/26 |
| 787976 | 12/1957 | (GB) | . |
| 2 167 416 | 5/1986 | (GB) | ............................. C07B/41/00 |
| WO 93/20034 | 10/1993 | (WO) | ............................. C07C/45/74 |

OTHER PUBLICATIONS

Translation of European Patent (UK) No. 0,449,071, Apr. 19, 1995, 17 pages.

(List continued on next page.)

*Primary Examiner*—Kathryn Gorgos
*Assistant Examiner*—Thomas H. Parsons
(74) *Attorney, Agent, or Firm*—Senniger, Powers, Leavitt & Roedel

(57) ABSTRACT

The invention proposes a process and waste treatment plant for regenerating alkali metal hydroxide (3) from an alkaline aqueous waste stream (5) that contains alkali metal C3+ carboxylate byproduct. The waste stream (5) is acidified and the resulting liquour (9) is fed to a first distillation zone (12) to distil carboxylic acid and water. Alternatively, it is fed to a settling zone (14) from which an upper organic layer (16) is recovered as well as a lower aqueous phase (17; 104) which is fed to the first distillation zone. The overhead product (20) from the first distillation zone is condensed and separated into a carboxylic acid layer which is either purged (28) or fed (101) to the settling zone (25). The lower layer (32) of the condensate is redistilled and the water bottoms stream (47) is fed to the cathode compartment (60) of an electrolytic cell (58), while the bottoms stream (52) from the first distillation zone is supplied to the anode compartment (59). Inorganic acid (8) regenerated in the anode compartment is used to acidify the waste stream, while alkali metal hydroxide solution from the cathode compartment is recycled to the chemical production plant (1).

27 Claims, 3 Drawing Sheets

OTHER PUBLICATIONS

Translation of European Patent (UK) No. 0,426,649, Nov. 23, 1994, 23 pages.

Derwent World Patent Index (WPI) abstract for Japanese Patent Publication No. 5023676, 1993.

International Search Report of PCT/GB97/02922 (3 pages), 1998.

"Aquatech Membrane Technology for Recovery of Acid/Base Values from Salt Streams", K.N. Mani, Desalination, vol. 68 (2–3), pp. 149–166 (1988).*

"A Solution to Caustic/Chlorine Imbalance: Bipolar Membrane Electrolysis", M. Paleologou et al., Journal of Pulp and Paper Science, vol. 18 (4), pp. J138–J145 (Jul. 1992).*

"The Greem Potential of Electrochemistry", Chemical Engineering, vol. 99, (Nov. 1992), pp. 132–141).*

* cited by examiner

PROCESS AND PLANT FOR TREATING AN AQUEOUS WASTE STREAM CONTAINING AT LEAST ONE ALKALI METAL CARBOXYLATE

BACKGROUND OF THE INVENTION

1. Field of the Invention

This invention relates to a process for treating an aqueous waste stream from a chemical production plant, more particularly an aqueous waste stream which contains at least one alkali metal carboxylate containing at least 3 carbon atoms, to produce a solution of an alkali metal hydroxide for recycle to the chemical production plant. In addition, the invention relates to a waste treatment plant for carrying out such a process.

2. Description of the Related Art

A number of types of chemical production plants produce a waste stream which contains at least one alkali metal carboxylate containing at least 3 carbon atoms up to about 22 carbon atoms. Normally, such an alkali metal carboxylate is a salt of an aliphatic acid. Examples of such chemical production plants include aldolisation plants in which a saturated aliphatic aldehyde, such as n-butyraldehyde or n-valeraldehyde, is converted by aldolisation followed by dehydration to an unsaturated aldehyde containing twice as many carbon atoms as the starting aldehyde, for example, 2-ethylhex-2-enal from n-butyraldehyde or 2-propylhept-2-enal from n-valeraldehyde. In such a process, the starting aldehyde may contain also a minor amount of the corresponding isomeric aidehyde, for example, iso-butyraldehyde or, in the case of n-valeraldehyde, also iso-valeraldehyde (2-methylbutyraldehyde) and 3-methylbutyraldehyde. The aldolisation-dehydration products, such as 2-ethylhex-2-enal and 2-propylhept-2-enal, find use as intermediates in the production of important plasticiser alcohols, such as 2-ethylhexanol and 2-propylheptanol.

An aldolisation-dehydration process is typically conducted in the presence of an aqueous solution of an alkali metal hydroxide as catalyst. When the starting aldehyde is n-butyraldehyde the reaction proceeds as follows:

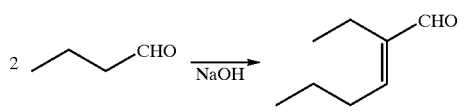

A competing reaction is the Cannizzaro reaction which yields a mixture of the alcohol corresponding to the starting aldehyde and an alkali metal salt of the corresponding carboxylic acid. Thus, if the catalyst is sodium hydroxide, the Cannizzaro reaction is:

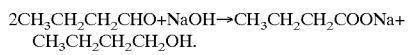

In order to limit the build up of the unwanted sodium carboxylate in the plant it is usual to purge a part of the aqueous liquor as a waste stream from the aldolisation plant. However, since this is alkaline and has a significant organic content, it cannot be discharged directly to the environment. Normally, the waste stream is neutralised and then subjected to appropriate biological treatment in order to reduce the oxygen demand of the waste stream to acceptable levels. The cost and inconvenience of importing to the plant site the acid used to neutralise the waste stream and the make up alkali needed to replace the alkali metal ions removed in the waste stream are drawbacks to the existing methods of operating an aldolisation plant. In addition, the capital cost of the necessary treatment plant required to reduce the oxygen demand to an acceptable level represents an undesirable additional expense, particularly since with increasing pressure to avoid pollution, plant operators are coming under increasing pressure to reduce the oxygen demand still further which requires even more capital expenditure.

Another process which produces an aqueous waste stream containing an alkali metal carboxylate is the conversion of iso-butyraldehyde to neopentyl glycol by reaction with formaldehyde. This proceeds by aldol condensation of formaldehyde with iso-butyraldehyde followed by a cross-Cannizzaro reaction between the intermediate β-hydroxyaldehyde, 2,2-dimethyl-3-hydroxypropanal, and formaldehyde according to the following equations:

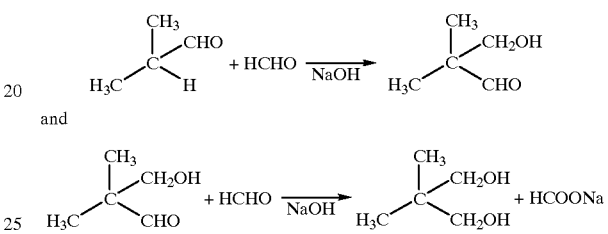

In this case, the aqueous waste stream contains sodium formate; in addition, it contains sodium iso-butyrate formed as a result of a Cannizzaro reaction from iso-butyraldehyde according to one of the following reactions:

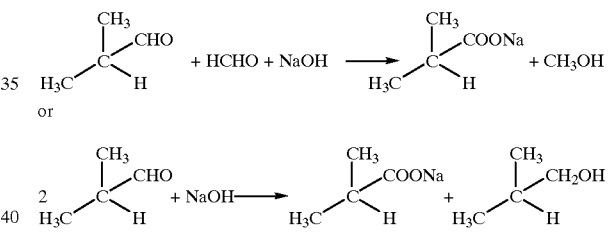

Another sodium salt in the waste liquor is sodium hydroxypivalate. This is formed by a Cannizzaro reaction of the intermediate β-hydroxyaldehyde, 2,2-dimethyl-3-hydroxypropanal, according to the following equation:

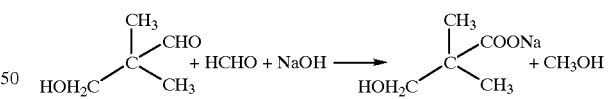

or according to the following equation:

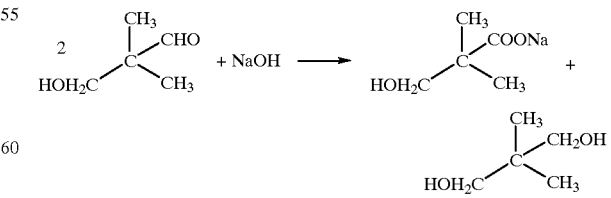

Again, this process is typically conducted using an alkali metal hydroxide or carbonate solution as catalyst.

Neopentyl glycol finds application in a range of technologies, including waterborne and alkyd surface coatings, gel coatings for fibreglass-reinforced plastics, powder coatings, lube oil additives, plasticisers and polyurethanes; the aldol product is produced without any dehydration step.

1,1,1-trimethylol propane is also of value, inter alia, in the production of alkyl resin coatings and can be produced by the aldol condensation of formaldehyde with n-butyraldehyde followed by hydrogenation. The aldolisation proceeds according to the following equations:

$$CH_3CH_2CH_2CHO+HCHO \rightarrow CH_3CH_2CH(CHO)CH_2OH$$

and $$CH_3CH_2CH(CHO)CH_2OH+HCHO \rightarrow CH_3CH_2C(CHO)(CH_2OH)_2.$$

These reactions can be catalysed by a solution of an alkali metal hydroxide, such as sodium hydroxide. The hydrogenation reaction is:

$$CH_3CH_2C(CHO)(CH_2OH)_2+H_2 \rightarrow CH_3CH_2C(CH_2OH)_3.$$

In a manner that is analogous to by-product formation in the synthesis of neopentyl glycol, there can be formed as byproducts by alkali-consuming side reactions, sodium butyrate, sodium formate and sodium 2,2-di (hydroxymethyl)-butyrate.

The conversion of 2,2-di(hydroxymethyl)-butyraldehyde to 1,1,1-trimethylol propane can be effected by a crossed Cannizzaro reaction using formaldehyde as the reducing agent in the presence of a basic catalyst. The reaction involved is:

$$CH_3CH_2C(CHO)(CH_2OH)_2+HCHO+NaOH \rightarrow \\ CH_3CH_2C(CH_2OH)_3+HCOONa.$$

In this case, at least one mole of sodium formate is produced per mole of neopentyl glycol produced.

Another important commercial chemical that finds its principal application in the surface coating industry as a raw material for oil-modified alkyd resins and synthetic drying oils is pentaerythritol. This can be produced by successive aldolisation steps followed by a hydrogenation or cross-Cannizzaro step, the starting materials being formaldehyde and acetaldehyde. The reactions involved are:

$$CH_3CHO+HCHO \rightarrow HOCH_2CH_2CHO;$$

$$HOCH_2CH_2CHO+HCHO \rightarrow (HOCH_2)_2CH\text{---}CHO;$$

and $$(HOCH_2)_2CH\text{---}CHO+HCHO \rightarrow (HOCH_2)_3C\text{---}CHO.$$

There then follows either:

$$(HOCH_2)_3CH\text{---}CHO+HCHO+NaOH \rightarrow (HOCH_2)_4C+HCOONa;$$

or $$(HOCH_2)_3CH\text{---}CHO+H_2 \rightarrow (HOCH_2)_4C.$$

A still further important commercial chemical is 2,2,4-trimethyl-1,3-pentanediol which is used, inter alia, as an intermediate in the production of unsaturated polyesters. This can be produced by aldolisation (or, as it may alternatively be termed, aldo-trimerisation) of iso-butyraldehyde followed by hydrogenation of the resulting intermediate aldolisation product, 2,6-di-iso-propyl-5,5-dimethyl-1,3-dioxan-4-ol, according to the following equations:

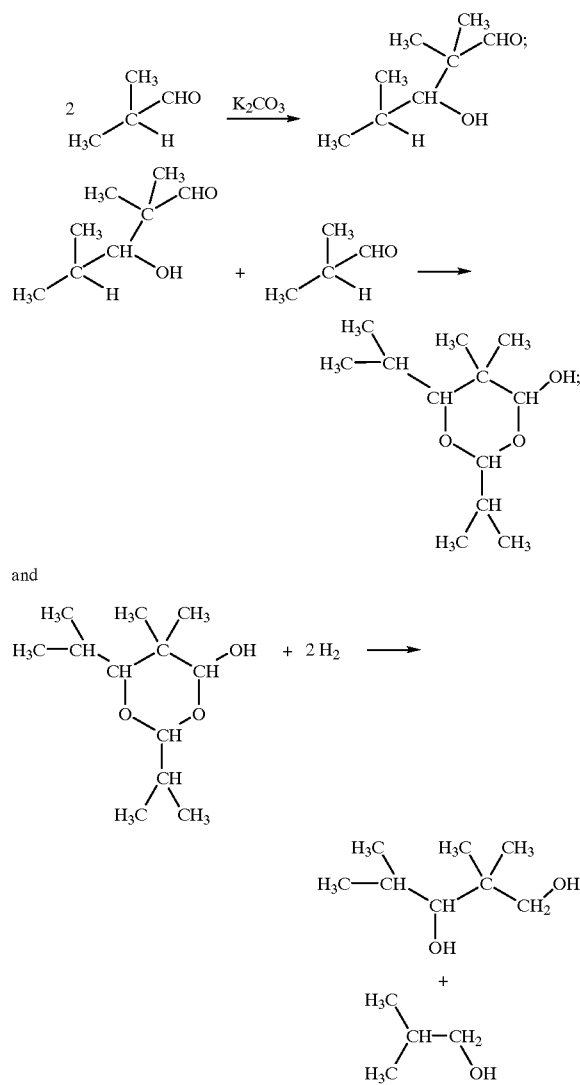

Certain hydrocarbon streams, for example $C_{10}$ to $C_{12}/C_{13}$ olefin streams produced by the reaction of carbon monoxide and hydrogen according to the Fischer-Tropsch process, contain oxygenated materials such as carboxylic acids and phenolic materials. These acids and phenolic materials can be removed by washing with dilute aqueous alkali.

Another industrial process which produces an alkaline waste stream is esterification. Organic carboxylic acid ester streams produced in commercial esterification plants are often washed with aqueous alkali in order to remove any unreacted organic carboxylic acids.

Production of all of the above mentioned commercial chemicals results in formation of an alkaline waste stream containing at least one alkali metal carboxylate, usually a sodium carboxylate. In each case, neutralisation and biological treatment are the methods of choice in order to render the waste stream fit for discharge to the environment. Nevertheless, the waste stream will still contain sodium or other alkali metal values which may not always be acceptable, for example, if it is intended that the treated waste stream is to be used for irrigation of crops. Moreover, in each case, it is necessary to import acid to the plant for the purpose of neutralisation and also make up quantities of sodium hydroxide or carbonate in order to replace the sodium values lost in the waste liquor.

An industrial process which produces an alkaline waste stream containing organic matter is the so-called Kraft process which is widely used in the wood pulp industry. In a typical procedure for treating such a waste stream, the sodium-containing waste liquor is concentrated and combusted in a furnace which is designed for burning the organic part of the sodium salts and for reduction of sulphur-containing salts to sodium sulphide. Sodium hydroxide is recovered by treating the green liquor product from the furnace melt with lime so as to convert sodium carbonate to sodium hydroxide and calcium carbonate. For further details of such a procedure reference may be made to a paper entitled "A simple integrated liquor preparation system" by J. F. Kuehl, Proceedings of the Symposium on Recovery of Pulping Chemicals held in Helsinki, May 13 to 17, 1988, pages 523 to 551.

Although solutions containing alkali metal carboxylates are amenable to treatment by similar methods to that described by J. F. Kuehl, the drawbacks are that the sodium hydroxide so produced is generally of low purity and that the process is costly not only in terms of fuel usage but also in terms of equipment costs.

It has been suggested in "The Green Potential of Electrochemistry", Engineering Practice, November 1992, pages 132 to 141 by D. Pletcher and N. L. Weinberg to use electrolysis cells to treat effluents. This paper mentions the need for technology to convert sodium salts back into sodium hydroxide.

The use of bipolar membrane technology for recovery of acid/base values from salt streams which are routinely generated in processing operations such as metal pickling, rayon manufacture, flue gas scrubbing, and fermentation is described in a paper entitled "Aquatech Membrane Technology for Recovery of Acid/Base Values from Salt Streams" by K. N. Mani et al., Desalination, Vol. 68 (2–3), pages 149 to 166 (1988). Table I of this paper lists various technology applications to which the technique can be applied.

EP-A-0096239 and U.S. Pat. No. 4,504,373 disclose an electrodialytic water splitting process for conversion of alkali metal sulphate values derived from spent rayon spin baths.

Conversion of alkali metal salts such as sodium sulphate or sodium phosphate into useful industrial feedstocks such as sulphuric acid and phosphoric acid by electrolysis in a membrane cell is described in U.S. Pat. No. 4,561,945.

In GB-A-787976 there is taught electrolytic decomposition of salts of organic aliphatic acids using a multicompartment cell having an anode compartment, a second compartment to contain the organic aliphatic acid resulting from electrolysis and, a cathode compartment, with appropriate permselective membranes between the compartments. One of the objectives of the process is to avoid treating the salts with a mineral acid.

Various specifications describe processes for effecting electrolysis of sodium sulphate to produce sulphuric acid and sodium hydroxide including EP-A-0426649, EP-A-0449071, EP-A-0531999, EP-A-0532188, and U.S. Pat. No. 3,134,729.

Production of sodium hydroxide and ammonium sulphate from sodium sulphate by an electrolysis technique is taught in U.S. Pat. No. 5,098,532.

Splitting of sodium sulphate into sodium hydroxide and sulphuric acid using bipolar membrane electrolysis is described in a paper entitled "A Solution to Caustic/Chlorine Imbalance: Bipolar Membrane Electrodialysis" by M. Paleologou et al., Journal of Pulp and Paper Science, Vol. 18, No. 4 (July 1992), pages J138 to J145.

U.S. Pat. No. 4,041,129 teaches a process for treating an acidic feed gas, such as a refinery gas, natural gas, or cracked gas, which contains $H_2S$, $CO_2$, COS, low molecular weight mercaptans or mixtures thereof. The process involves washing the acidic feed gas with a solution containing sodium hydroxide and sodium sulfate. The reaction effluent is passed through an extraction or adsorbent unit in order to remove organic impurities It then passes into a reaction chamber in which it is contacted with a solution containing sulfuric acid and sodium sulfate. The resulting treated liquid is passed to an acidic gas stripper which removes $CO_2$ and $H_2S$ therefrom. The liquor from the acidic gas stripper is fed to the middle compartment of a three compartment electrolytic cell. The solutions used for washing the acidic feed gas and for reaction with the effluent are taken from the relevant electrolyte compartments.

GB-A-216741 proposes oxidation of an organic compound with an alkali hypohalite in an aqueous medium, separating the oxidized organic compound from waste fluid containing alkali halogenide, subjecting the waste fluid to electrolysis to produce alkali hydroxide and halogen, reacting the alkali hydroxide with halogen to produce alkali hypohalite, and recycling the alkali hypohalite as the oxidizing agent. The oxidized compound can be a carboxylic acid when the oxidizable compound is an aldehyde.

The Derwent Abstract of JP-A-05023676 proposes treatment of a waste liquor containing ammoniacal nitrogen and/or organic acid by adjusting the pH to below 6, distilling to separate solid and liquid, and electrolysing using a platinum electrode.

U.S. Pat. No. 4,752,363 is concerned with effluent treatment where the effluent contains sodium hydroxide from, for example, a textile treatment process, as well as multivalent ions and soluble and insoluble organic and inorganic matter. The process involves pH adjustment using an acid gas, followed by filtration. The filtrate is subjected to electrolysis.

In EP-A-0631988 there is proposed a process for the purification of effluents from the aidolisation reaction characterised in that the effluent is adjusted to a pH value of 0 to 6 and an organic phase which thereby separates out is optionally separated and the effluent finally extracted with monoalcohols which contain 8 or more carbon atoms in the molecule and/or with hydrocarbons which contain more than 6 carbon atoms in the molecule.

It would be desirable to provide a process for treating these and other alkaline process waste streams containing an alkali metal carboxylate or carboxylates which avoids the consumption of an acid for neutralisation. It would further be desirable to provide a process for treating an alkaline waste liquor containing at least one alkali metal carboxylate which results in essentially no loss of alkali metal values from the process and accordingly obviates substantially the need to provide make up quantities of alkali to replace alkali metal values lost from the plant.

SUMMARY OF THE INVENTION

The present invention accordingly seeks to provide a process for treatment of aqueous alkaline waste streams containing an alkali metal carboxylate or carboxylates which avoids the consumption of an acid for neutralisation. It further seeks to provide a process for treating an alkaline waste liquor containing at least one alkali metal carboxylate which results in essentially no loss of alkali metal values from the process and accordingly obviates substantially the need to provide make up quantities of alkali to replace alkali metal values lost from the plant.

DETAILED DESCRIPTION OF THE INVENTION

According to the present invention there is provided a process for treating an aqueous waste stream from a chemical production plant, which aqueous waste stream contains at least one alkali metal carboxylate containing at least 3 carbon atoms, to produce a solution of an alkali metal hydroxide for recycle to the chemical production plant, which process comprises:

(a) admixing the waste stream with a dilute aqueous solution of an inorganic acid selected from phosphoric acid, sulphuric acid, or a mixture thereof so as to generate from said at least one alkali metal carboxylate a corresponding carboxylic acid or acids and to produce an acidic liquor having a pH of less than about 3.5 and containing an alkali metal salt of the inorganic acid;

(b) separating free carboxylic acid or acids from the acidic liquor of step (a) to form an acidic predominantly aqueous phase containing the alkali metal salt of the inorganic acid;

(c) providing an electrolysis zone comprising an anode compartment and a cathode compartment, the anode compartment containing an anode and the cathode compartment containing a cathode, and the anode compartment being separated from the cathode compartment by means of an ion permeable membrane permeable to alkali metal ions;

(d) supplying the acidic predominantly aqueous phase resulting from step (b) to the anode compartment of the electrolysis zone;

(e) supplying water to the cathode compartment of the electrolysis zone;

(f) passing a current between the anode and the cathode thereby to subject the acidic predominantly aqueous phase to electrolysis, to cause alkali metal ions to pass through the ion permeable membrane from the anode compartment to the cathode compartment and form alkali metal hydroxide therein, and to regenerate inorganic acid in the anode compartment;

(g) recovering from the cathode compartment an alkali metal hydroxide solution for recycle to the chemical production plant; and (h) recycling a solution containing the inorganic acid produced in step (f) to step (a).

In such a process, the chemical production plant may be an aldolisation plant in which a saturated aliphatic aldehyde containing at least 3 carbon atoms is subjected to aldolisation and dehydration in the presence of an alkali catalyst selected from an alkali metal hydroxide and an alkali metal carbonate to form an unsaturated aldehyde containing twice as many carbon atoms as the saturated aliphatic aldehyde. The saturated aliphatic aldehyde can be n-butyraldehyde or n-valeraldehyde, in which case the unsaturated aldehyde is 2-ethylhex-2-enal or 2-propylhept-2-enal.

Alternatively, the chemical production plant can be a plant for converting iso-butyraldehyde to neopentyl glycol by reaction with formaldehyde in the presence of an alkali catalyst selected from an alkali metal hydroxide and an alkali metal carbonate.

It can alternatively, be a chemical production plant for the production of 1,1,1-trimethylolpropane, pentaerythritol, or 2,2,4-trimethyl-1,3-pentanediol which uses an appropriate process as described above.

The chemical production plant may be a hydrocarbon washing plant, for example, a plant for washing with a dilute solution of sodium hydroxide a hydrocarbon stream produced by the Fischer-Tropsch process.

Alternatively, the chemical production plant can be an esterification plant for the production of, for example, a maleic acid ester, such as dimethyl maleate or diethyl maleate, a phthalic acid ester, such as dimethyl terephthalate, or a methyl ester of one or more higher aliphatic carboxylic acids such as are used in the production of so-called natural detergent alcohols, e.g. a methyl ester of a $C_8$ to $C_{22}$ aliphatic carboxylic acid or a mixture or two or more thereof.

The waste stream from such a chemical production plant may contain, for example from about 5 g/l up to about 300 g/l of alkali metal carboxylate salts, typically from about 50 g/l to about 150 g/l, e.g. about 100 g/l.

Because the process of the present invention regenerates alkali metal hydroxide so that essentially no alkali metal values are lost from the plant in the treated waste liquor, it becomes possible not only to utilise sodium hydroxide or sodium carbonate as catalyst in the chemical production plant, but also the more expensive alkali metal hydroxides and carbonates, for example the hydroxides and carbonates of lithium, potassium, rubidium, and caesium. The use of such more expensive alkali metal hydroxides may be desirable in cases where their solubility properties would be an advantage in operation of the chemical production plant. Normally, however, it will be preferred to utilise sodium hydroxide or sodium carbonate as catalyst in the chemical production plant.

The process of the invention generates a solution of an alkali metal hydroxide; this can, if desired, be converted to the corresponding carbonate by reaction with carbon dioxide.

In the process of the invention step (b) can include subjecting the acidic liquor to distillation in a first distillation zone maintained under distillation conditions effective for distillation of free carboxylic acid and water from the acidic liquor to form the acidic predominantly aqueous phase. Such a procedure is applicable, in particular, when the free carboxylic acid, e.g. propionic acid or n-butyric acid, is relatively water-soluble and forms an azeotropic mixture with water which condenses to form a single phase condensate. In this case, there can be recovered from the first distillation zone an overhead product comprising the carboxylic acid or acids and water, as well as possibly also minor organic by-products; this overhead product can be condensed and allowed to separate to form an organic layer comprising minor organic by-products which are purged and an aqueous liquid containing free carboxylic acid or acids.

When the free carboxylic acid has low water solubility it is alternatively possible for step (b) to include passing the acidic liquor to a settling zone (optionally after addition of a substantially water-insoluble solvent), recovering from the settling zone an organic phase comprising free carboxylic acid (and any added substantially water-insoluble solvent) and an aqueous phase, and subjecting the aqueous phase to distillation in a first distillation zone maintained under distillation conditions effective for distillation of free carboxylic acid and water from the acidic liquor to form the acidic predominantly aqueous phase. In this case, there can be recovered from the first distillation zone an overhead product comprising the carboxylic acid or acids and water; such an overhead product may be condensed and allowed to separate to form an organic layer comprising free carboxylic acid or acids which is recycled to the settling zone and an aqueous liquid.

Addition of a solvent which is incompletely soluble in water, preferably a substantially water-insoluble solvent, may be desirable in cases in which the free carboxylic acid has an appreciable solubility in water. In this case, addition of the solvent facilitates the separation and extraction of the liberated free carboxylic acid into the organic phase in the settling zone. When the solvent has limited solubility in water, the presence of the inorganic salts in the aqueous phase will reduce the solubility in the aqueous phase of a solvent that is partially soluble in water, such as iso-butanol, thereby enhancing phase separation.

Suitable solvents include aliphatic hydrocarbons, such as hexane; aromatic hydrocarbons, such as toluene; aliphatic alcohols, such as n-butanol, iso-butanol, and 2-ethylhexanol; phenols, such as phenol, o-cresol, m-cresol, p-cresol, and mixtures thereof; ethers, such as diethyl ether, di-iso-propyl ether and ethyl phenyl ether; higher aliphatic organic acids containing from about 6 to about 14 carbon atoms, such as caproic acid, caprylic acid, decanoic acid, and mixtures thereof; aldehydes, such as n-butyraldehyde, 2-ethylhex-2-enal, and the like; trimers of aldehydes formed by aldolisation, such as the trimer of n-butyraldehyde of the formula:

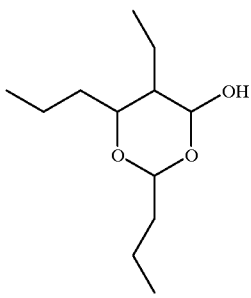

and the like; esters, such as n-butyl n-butyrate; chlorinated hydrocarbons, such as carbon tetrachloride, ethylene dichloride, and chloroform; and the like.

Any added solvent can be separated from the organic layer from the settling zone by conventional means, such as distillation, and recycled, if desired.

At least a part of the aqueous liquid recovered from the first distillation step may be subjected to a second distillation step in a second distillation zone maintained under distillation conditions effective for distillation of a mixture of water and free carboxylic acid from a bottoms stream comprising substantially pure water. This bottoms stream may be passed to the cathode compartment. It is also envisaged that the bottoms stream can be admixed with liquor recycled from the cathode compartment to form a mixed feed stream for admission to the cathode compartment. This mixed feed stream is desirably pumped through the cathode compartment at a rate sufficient to sweep at least a majority of the gas bubbles generated by electrolysis off the surface of the cathode substantially as fast as they are formed.

The acidic predominantly aqueous phase can be admixed with liquor recycled from the anode compartment to form a mixed acidic liquor for admission to the anode compartment. This mixed acidic liquor is preferably pumped through the anode compartment at a rate sufficient to sweep at least a majority of the gas bubbles generated by electrolysis off the surface of the anode substantially as fast as they are formed.

The rates of pumping through the anode and cathode compartments are preferably sufficiently high to sweep off the surface of the anode or cathode, as the case may be, at least about 90% or more, and preferably all, of the gas bubbles generated by electrolysis substantially as fast as they are formed. In general, the higher that the rate of pumping is, the higher will be the liquid velocity over the electrode surface and thus the more efficient that removal of gas bubbles will be. This will result in less of the electrode surface being covered with gas bubbles and hence will increase the percentage of the area of the electrode that is in conductive contact with the solution in the electrode compartment. Furthermore the electrode compartment is desirably designed so as to eliminate "dead space" where static pockets of liquid can occur. Preferably, the anode and cathode compartments are each designed so that the liquid is pumped through the respective compartment in a direction substantially parallel to and in close proximity to the electrode surface or at a small angle thereto, e.g. about 30° or less. In this way, the efficiency with which gas bubbles are swept off the electrode as they are formed will be maximized. If the electrode is in the form of a plate, then the electrode compartment is conveniently constructed with the ion permeable membrane arranged substantially parallel to a major face of the electrode and relatively closely spaced therefrom so that a passage for the circulating liquid is formed between the ion permeable membrane and the electrode. A similar space can be left between the other major face of the electrode and a wall of the electrode compartment through which the circulating liquid can also be passed. It is also possible to provide an ion permeable membrane adjacent each major face of the electrode so that an anode compartment lies between two cathode compartments or a cathode compartment lies between two anode compartments. Moreover it is possible to construct a bank of electrode compartments with alternating anode and cathode compartments, each separated from an adjacent electrode compartment by means of an ion permeable membrane.

Any known ion permeable membrane can be used, for example, the membranes sold as NAFION™ membranes.

In the process of the invention, it will normally be preferred to recycle solution through the cathode compartment until the concentration of alkali metal hydroxide has built up to a sufficient strength for recycle to the chemical production plant. Typically, the alkali metal hydroxide concentration in the solution circulating through the cathode compartment is in. the range of from about 10 to about 250 g/l, more usually from about 20 to 200 g/l, e.g. about 50 g/l. It will further often be preferred to select an alkali metal concentration in the solution circulating through the cathode compartment such that the quantity of water in the solution recycled to the chemical production plant provides the net quantity of water in the waste stream withdrawn from the chemical production plant, i.e. the total quantity of water in the waste stream less any water produced in the chemical production plant. In this way, the waste treatment process of the present invention can be used to maintain the correct water balance in the chemical production plant. In the event that any water is lost in a stream discharged from the waste treatment plant, then a corresponding amount of water can be added to the solution circulating through the cathode compartment in order to return to the chemical production plant in the alkali metal hydroxide recycle stream a quantity of water equivalent to that present in the waste stream being treated.

A dilute aqueous solution containing phosphoric acid, sulphuric acid or a mixture thereof is used in step (a) of the process of the present invention. This needs to be in amounts sufficient to bring the pH, after mixing with the aqueous waste stream, to 3.5 or lower. Typically, the pH following addition of the solution of inorganic acid to the waste stream is from about 2 to about 3.5, preferably from about 3 to 3.5.

It is desirable not to lower the pH of the solution too far below that corresponding to the pKa of the carboxylic acid in order to minimize the risk of corrosion of the plant. A typical acid concentration for the solution of sulphuric acid, phosphoric acid or a mixture thereof is from about 10 to about 200 g/l, more usually from about 40 to about 75 g/l, e.g. about 50 g/l. The anode compartment solution can be recycled a sufficient number of times until an acid concentration in this range is achieved.

The first and second distillation zones can be operated under reduced or elevated pressure, for example at a pressure in the range of from about 0.01 bar up to about 10 bar. Conveniently they are operated at about 1 bar, i.e. at atmospheric pressure. The overhead temperature in the column comprising the respective distillation zone is high enough for the requisite overhead product, whether an azeotrope or not, to be at or above its boiling point at the top of that column at the operating pressure of that distillation column. Typically, this temperature will range from about 80° C. to about 140° C. The first and second distillation zones can be operated at the same or different pressures.

In the process of the invention, the free carboxylic acid or acids can be recovered in most cases as an organic phase. Exceptions include cases when the carboxylic acid comprises n-butyric acid or propionic acid. Since formic acid forms an azeotrope with water whose boiling point (107.1° C.) is higher than that of water and since acetic acid does not form an azeotrope with water, the process is restricted to treatment of aqueous waste streams containing an alkali metal carboxylate or carboxylates derived from carboxylic acids having 3 or more carbon atoms, for example from 3 to 22 carbon atoms.

Phase separation is effected in suitable settling zones such as decanters.

In the process of the invention, the electrolysis zone is preferably operated at a temperature of from about 15° C. to about 90° C. Moreover the current strength used in step (f) typically ranges from about 500 to about 5000 amps/m$^2$, more usually in the range of from about 1500 to about 4000 amps/m$^2$, preferably from about 2000 to about 3500 amps/m$^2$, of electrode area. A stainless steel cathode can be used. The anode preferably consists of or is coated with $IrO_2$ or an $IrO_2/Ta_2O_5$ mixture. Titanium, a titanium alloy, and titanium clad with a so-called conducting ceramic are suitable materials from which to make anodes suitable for coating with, for example, $IrO_2$ or an $IrO_2/Ta_2O_5$ mixture.

Since the solution supplied to the anode compartment is acidic it will contain only trace amounts of free carboxylate ions. Thus there is little possibility of the Kolbe reaction occurring. In the Kolbe reaction, i.e.:

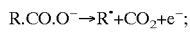

and

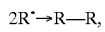

organic free radicals are formed (except in the case of formate ions). Such free radicals can attack and destroy the anode itself, causing undesirable corrosion of its surface. Hence, the life of most anode materials is relatively short during operation under Kolbe reaction conditions. On the other hand, anodes used in the process of the present invention enjoy a long life since they are not subject to corrosion due to attack by organic free radicals.

The invention further provides a waste treatment plant ror treating an aqueous waste stream from a chemical production plant, which aqueous waste stream contains at least one alkali metal carboxylate containing at least 3 carbon atoms, to produce a solution of an alkali metal hydroxide for recycle to the chemical production plant, the waste treatment plant comprising:

(a) means for admixing the waste stream with a dilute aqueous solution of an inorganic acid selected from phosphoric acid, sulphuric acid, or a mixture thereof so as to generate from said at least one alkali metal carboxylate a corresponding carboxylic acid or acids and to produce an acidic liquor having a pH of less than about 3.5 and containing an alkali metal salt of the inorganic acid;

(b) means for separating free carboxylic acid or acids from the acidic liquor of step (a) to form an acidic predominantly aqueous phase;

(c) an electrolysis zone comprising an anode compartment and a cathode compartment, the anode compartment containing an anode and the cathode compartment containing a cathode, and the anode compartment being separated from the cathode compartment by means of an ion permeable membrane permeable to alkai metal ions;

(d), means for supplying the acidic predominantly aqueous phase to the anode compartment of the electrolysis zone;

(e) means for supplying water to The cathode compartment of the electrolysis zone;

(f) means for passing a current between the anode and the cathode thereby to subject the acidic predominantly aqueous phase to electrolysis, to cause alkali metal ions pass through the ion permeable membrane from the anode compartment to the cathode compartment and form alkali metal hydroxide therein, and to regenerate inorganic acid in the anode compartment;

(g) means for recovering from the cathode compartment an alkali metal hydroxide solution for recycle to the chemical production plant;

(h) means for recycling a solution containing the inorganic acid produced in the anode compartment to the admixing means (a); and (i) means for recovering the liquid stream of free carboxylic acid or acids separated in the separating means (b).

In the waste treatment plant of the invention the means for separating free carboxylic acid or acids from the acidic liquor of step (a) to form an acidic predominantly aqueous phase may comprise a first distillation zone maintained under distillation conditions effective for distillation of free carboxylic acid and water from the acidic liquor to form the acidic predominantly aqueous phase. Moreover, the first distillation zone can include means for condensing an overhead product comprising the carboxylic acid or acids and condensing an upper layer comprising free carboxylic acid or acids and a lower aqueous liquid, and means for purging the resulting upper layer from the waste treatment plant.

Furthermore, the means for separating free carboxylic acid or acids from the acidic liquor of step (a) to form an acidic predominantly aqueous phase can comprise a settling zone, means for recovering from the settling zone an organic phase comprising free carboxylic acid and an aqueous phase, and a first distillation zone maintained under distillation conditions effective for distillation of free carboxylic acid and water from the aqueous phase. The first distillation zone preferably includes means for condensing an overhead product comprising the carboxylic acid or acids and water, settling means for separating from the resulting condensate an organic layer comprising free carboxylic acid or acids and an aqueous liquid, and means for recycling the resulting organic layer to the settling zone.

The waste treatment plant preferably includes a second distillation zone maintained under distillation conditions effective for distillation from the aqueous liquid recovered from the first distillation step of a mixture of water and free carboxylic acid and to form a bottoms stream comprising substantially pure water. In this case, the means for supplying water to the cathode compartment of the electrolysis zone conveniently comprises means for passing the bottoms stream from the second distillation zone to the cathode compartment. The waste treatment plant preferably further includes means for admixing the bottoms stream with liquor recycled from the cathode compartment to form a mixed feed stream for admission to the cathode compartment. In this case, the means for passing the bottoms stream from the second distillation zone to the cathode compartment can include a pump adapted to pump the mixed feed stream through the cathode compartment at a rate sufficient to sweep at least a majority of the gas bubbles generated by electrolysis off the surface of the cathode substantially as fast as they are formed.

In one form of waste treatment plant according to the invention, the means for supplying the acidic predominantly aqueous phase to the anode compartment of the electrolysis zone comprises means for admixing the acidic predominantly aqueous phase with liquor recycled from the anode compartment to form a mixed acidic liquor for admission to the anode compartment. In this case, the means for supplying the acidic predominantly aqueous phase to the anode compartment of the electrolysis zone further includes a pump for pumping mixed acidic liquor through the anode compartment at a rate sufficient to sweep at least a majority of the gas bubbles generated by electrolysis off the surface of the anode substantially as fast as they are formed.

BRIEF DESCRIPTION OF THE DRAWINGS

In order that the invention may be clearly understood and readily carried into effect some preferred forms of a plant for the treatment of an aqueous waste stream containing at least one alkali metal carboxylate, which are each designed to operate according to the teachings of the invention, will now be described, by way of example only, with reference to the accompanying drawings, in which.

It will be understood by those skilled in the art that, as the drawings are diagrammatic, only the most important items of equipment have been depicted, for the sake of simplicity, and that other items of equipment, such as pumps, holding tanks, flow control valves, liquid flow meters, level controllers, temperature controllers, voltage regulators and the like would be required in an operational plant.

DETAILED DESCRIPTION OF THE DRAWINGS

Figure 1:
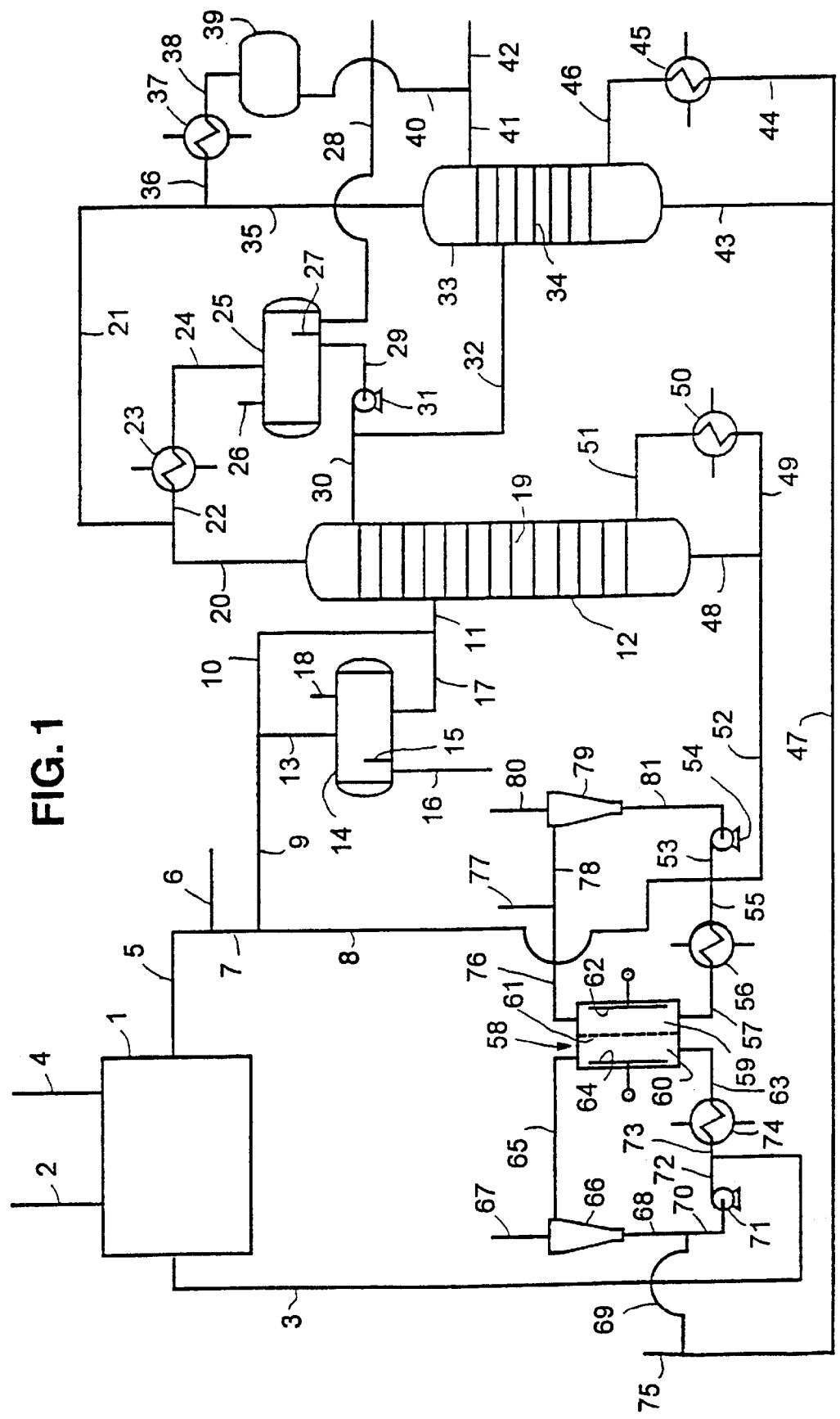
FIG. 1 is a flow diagram of a plant for the recovery from an aqueous waste stream from a chemical plant, for example an aldolisation plant used for the production of 2-ethylhex-2-enal from n-butyraldehyde, of a sodium hydroxide solution for re-use in the aldolisation process.

Referring to FIG. 1 of the drawings, a chemical production plant 1, which uses an alkali metal hydroxide as catalyst, is supplied in line 2 with a feedstock. For the purposes of the following description, the plant 1 is an aldolisation plant and the feedstock is an aldehyde, such as n-butyraldehyde. However, it will be appreciated by those skilled in the art that the plant 1 can be any of a variety of types of chemical plants which requires an aqueous solution of an alkali as catalyst and produces an aqueous alkaline waste stream containing at least one alkali metal carboxylate derived from an organic carboxylic acid containing at least 3 carbon atoms up to, for example, 22 carbon atoms.

In plant 1 there is effected the production from n-butyraldehyde of 2-ethylhex-2-enal. Plant 1 is supplied in line 2 with a feedstock which, for the purpose of the following description, is n-butyraldehyde. However, the feedsLock can be another aldehyde, for example, n-valeraldehyde. Plant 1 is also fed with an aqueous recycle stream containing sodium hydroxide by way of line 3. Product 2-ethylhex-2-enal leaves plant 1 in line 4. For further description of a typical design for plant 1 the attention of the reader is directed to WO-A-93/20034. An aqueous waste stream containing sodium hydroxide and sodium salts of organic acids formed as a result of the Cannizzaro reaction:

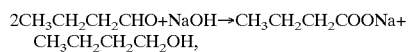

is recovered from plant 1 in line 5. Its principal organic acid salt component is sodium n-butyrate, although it may also contain other components such as the Cannizzaro reaction product from 2-ethylhex-2-enal, i.e. sodium 2-ethylhex-2-enoate.

Phosphoric acid is supplied to the waste stream in line 5 by way of line 6 in a sufficient quantity to reduce the pH of the resulting solution in line 7 to 3.3 or below. The residual sodium hydroxide in the waste stream in line 5 is thereby converted to monosodium dihydrogen phosphate, while the sodium n-butyrate and other sodium salts of organic acids are also converted to the same inorganic salt and to the corresponding organic acid. Hence the solution in line 7 comprises free n-butyric acid, possibly traces of other organic acids, monosodium dihydrogen phosphate, minor organic impurities, a small amount of free phosphoric acid, and minor amounts of other phosphates.

The solution in line 7 is mixed with recycled material from line 8 and sent forward in lines 9, 10, and 11 to distillation column 12. (Alternatively, if the plant 1 uses a higher aldehyde as feedstock so that solution in line 9 contains a relatively involatile material, or a material that has very low solubility in water, all or a part of the material in line 9 can be diverted by way of line 13 to a decanter 14 in which it can separate out into two layers; an upper organic layer, comprising mainly organic acids, overflows weir 15 and can be recovered in line 16 for further treatment or for disposal by incineration, the lower aqueous phase flowing on in line 17 to join the stream in line 10, while reference numeral 18 indicates a vent line from decanter 14).

Distillation column 12 contains trays 19; alternatively it can contain column packing of conventional design. A mixture of steam, n-butyric acid, and minor amounts of other organic impurities, which approaches the azeotropic composition, is recovered overhead from distillation column 12 in line 20. This is combined with an azeotropic vaporous stream comprising water and n-butyric acid from line 21 (the origin of which is described further below) and the combined stream flows on in line 22 to condenser 23. The resulting condensate passes in line 24 to decanter 25 which is provided with a vent line 26 and an internal weir 27. Any water-insoluble condensed organic material that collects in decanter 25 overflows weir 27 and exits the plant in line 28. Since this material is substantially free from sodium ions, it can be passed on for disposal by incineration.

The aqueous layer that collects in decanter 25 contains n-butyric acid; part is recycled in lines 29 and 30 by means of pump 31 to an upper part of distillation column 12 as a reflux stream. The remainder is passed in line 32 to a second distillation column 33 equipped with trays 34 (or packing). An azeotropic mixture of steam and n-butyric acid exits the top of second distillation column 33 in line 35; part forms the vaporous stream in line 21, while the remainder travels on in line 36 to condenser 37. The condensate from condenser 37 is fed in line 38 to condensate drum 39; a major part is recycled from condensate drum 39 to an upper part of second distillation column 33 as reflux stream by way of lines 40 and 41, while the remainder, which is essentially free from sodium ions and whose composition is essentially that of the n-butyric acid/water azeotrope, is purged from the plant in line 42.

From the bottom of second distillation column 33 there is recovered in line 43 a stream consisting essentially of water with trace amounts of n-butyric acid. Part of this stream is recycled in line 44 to a reboiler 45 and then returned to second distillation column 33 in line 46. The rest is fed to line 47.

From the bottom of distillation column 12 is removed in line 48 a stream consisting essentially of an aqueous solution of sodium phosphate with only minor amounts of n-butyric acid and other organic impurities. Part of this stream is recycled to column 12 by way of line 49, column reboiler 50, and line 51. The remainder is discharged from column 12 in line 52. This is mixed with a recirculating stream in line 53 from pump 54. The major portion of the mixed stream in line 55 continues on in line 55 and is cooled in passage through heat exchanger 56 which is supplied with cooling water; the remainder forms the stream in line 8.

The cooled stream from heat exchanger 56 continues in line 57 to an electrolysis zone 58 which comprises an anode compartment 59 separated from a cathode compartment 60 by means of an ion permeable membrane 61 made, for example, from NAFION™ which is permeable to sodium ions (and to other alkali metal ions). An iridium oxide coated anode 62 is positioned in anode compartment 59. Dilute sodium hydroxide solution is supplied to the cathode compartment 60 in line 63; cathode compartment 60 contains a stainless steel cathode 64.

A direct current is supplied to electrolysis zone 58 between anode 62 and cathode 64, thereby causing sodium ions to migrate from the anode compartment across the membrane 61 to the cathode compartment 60, there to combine with hydroxide ions which are produced at cathode 64 by the discharge of hydrogen ions through electrolysis of water. Oxygen is produced at anode 62 to satisfy the overall ion balance. The rate of recycle of the stream in line 57 is sufficient to cause a high enough liquid velocity through anode compartment 59 to sweep at least a majority of the gas bubbles generated by electrolysis off the surface of anode 62 substantially as fast as they are formed. Similarly, the rate of supply of dilute sodium hydroxide solution from line 63 to cathode compartment 60 is sufficiently high to produce a liquid velocity through the cathode compartment that is high enough to perform a similar gas bubble sweeping function across the surface of cathode 64.

Liquid exiting cathode compartment 60 in line 65 enters a gas-liquid separator 66 which is provided with a gas vent 67. The degassed liquid in line 68 is mixed with a recycle stream from line 69; the ensuing mixed stream carries on in line 70 to pump 71 and passes in line 72 to a junction with line 3. Part of this flow thus forms the make up catalyst stream in line 3 for the aldolisation plant 1. The rest passes in line 73 to a heat exchanger 74, which is supplied with cooling water, to form the supply in line 63 to cathode compartment.

The stream in line 69 comprises the material in line 47; line 75 indicates a supply line for the supply of any necessary make up sodium hydroxide solution for plant 1.

A mixture of liquid and oxygen exits anode compartment 59 in line 76. The liquid component of this mixture comprises an aqueous solution of phosphoric acid, mono sodium dihydrogen phosphate and traces of n-butyric acid and other organic compounds. Air or nitrogen is optionally added by way of line 77 in order to dilute the oxygen. The resulting mixture flows on in line 78 to a gas-liquid separator 79 which is fitted with a gas vent 80. The gas-free liquid continues in line 81 to pump 54 to form the stream in line 53.

Once steady state operating conditions are achieved, the amount of acid generated in electrolysis zone 58 is equivalent to the total sodium hydroxide and sodium n-butyrate discharged from aldolisation plant 1 in line 5 and the amount of phosphoric acid added by way of line 6 need be only that amount that is required to replenish any process losses.

Since the sodium values in line 5 are converted to an equivalent amount of sodium hydroxide in line 3, it is only necessary to supply in line 75 a negligible amount of sodium hydroxide sufficient to compensate for losses of traces of sodium values from the plant.

Figure 2:
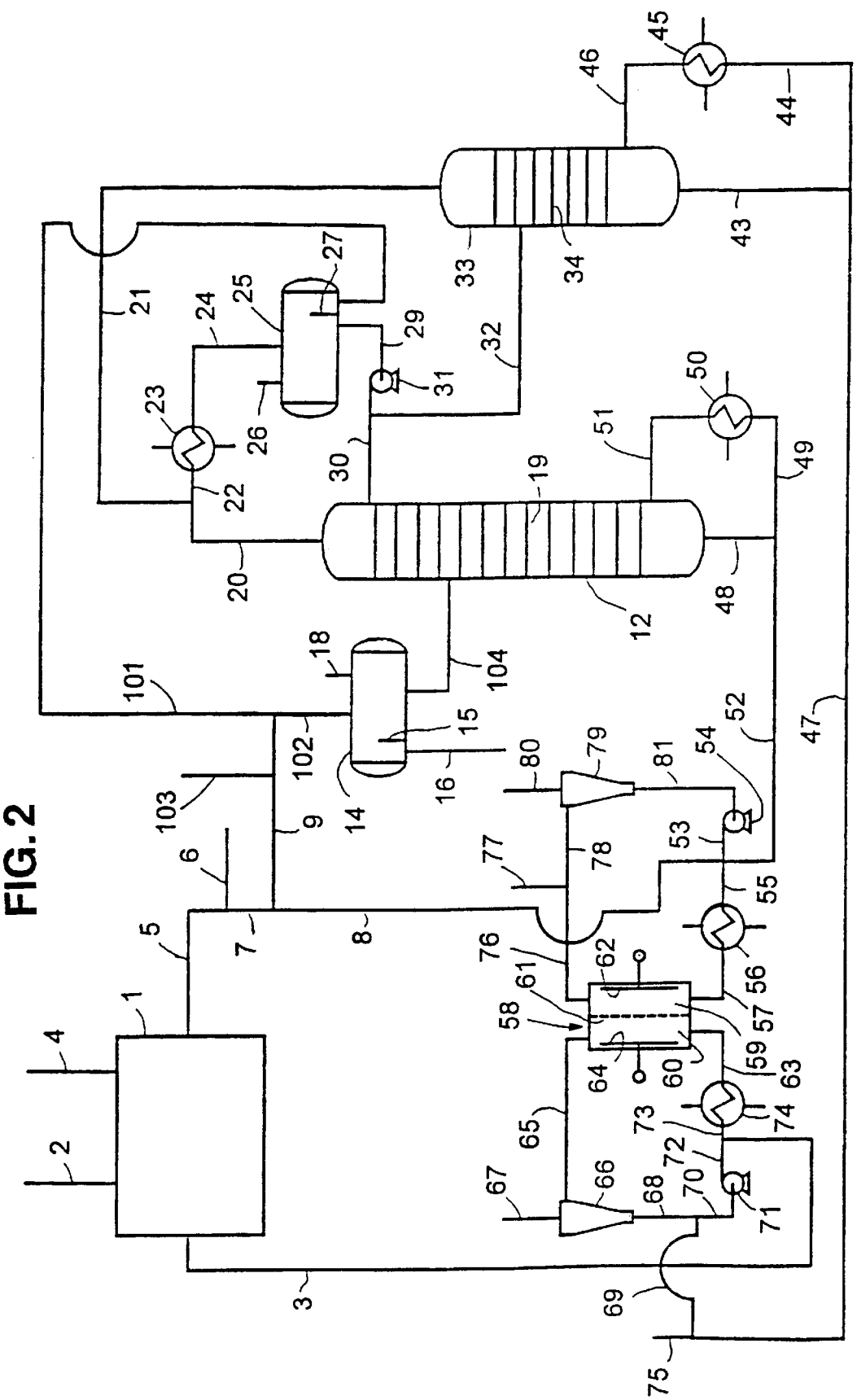
FIG. 2 is a flow diagram of a similar plant for treatment of an aqueous waste stream from a plant for converting iso-butyraldehyde to neopentyl glycol by reaction with formaldehyde.

The plant of FIG. 2 is generally similar in design to that of FIG. 1 and so like references have been used to indicate like pieces of equipment.

In FIG. 2 plant 1 is used for the production of neo-pentyl glycol by reaction of iso-butyraldehyde with formaldehyde. This proceeds by aldol condensation of formaldehyde with iso-butyraldehyde followed several purification steps. The material leaving plant 1 in line 5 comprises an aqueous solution containing sodium iso-butyrate and sodium hydroxypivalate. After mixing with aqueous phosphoric acid or sulphuric acid from line 8 the mixture flows on in line 9. It is then mixed with recycled organic material from line 101 and continues in line 102 to decanter 14. If desired, an organic substantially water-immiscible solvent can be added via line 103. Since the solubility of iso-butyric acid in a sodium sulphate solution is lower than in pure water, an organic layer is formed in decanter 14 into which the otherwise highly water-soluble hydroxypivalic acid is extracted. The organic layer overflowing weir 15 and purged in line 16 can be incinerated or otherwise disposed of or treated for recovery purposes. The aqueous layer is fed in line 104 to distillation column 12.

If a solvent is supplied in line 103 this can be, for example, selected from aliphatic hydrocarbons, such as hexane; aromatic hydrocarbons, such as toluene; aliphatic alcohols, such as n-butanol, iso-butanol, and 2-ethylhexanol; phenols, such as phenol, o-cresol, m-cresol, p-cresol, and mixtures thereof; ethers, such as diethyl ether, di-iso-propyl ether and ethyl phenyl ether; higher aliphatic organic acids containing from about 6 to about 14 carbon atoms, such as caproic acid, caprylic acid, decanoic acid, and mixtures thereof; aldehydes, such as n-butyraldehyde, 2-ethylhex-2-enal, and the like; trimers of aldehydes formed by aldolisation, such as the trimer of n-butyraldehyde of the formula:

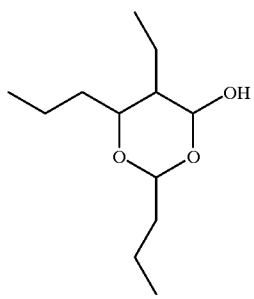

and the like; esters, such as n-butyl n-butyrate; chlorinated hydrocarbons, such as carbon tetrachloride, ethylene dichioride, and chloroform; and the like.

Figure 3:
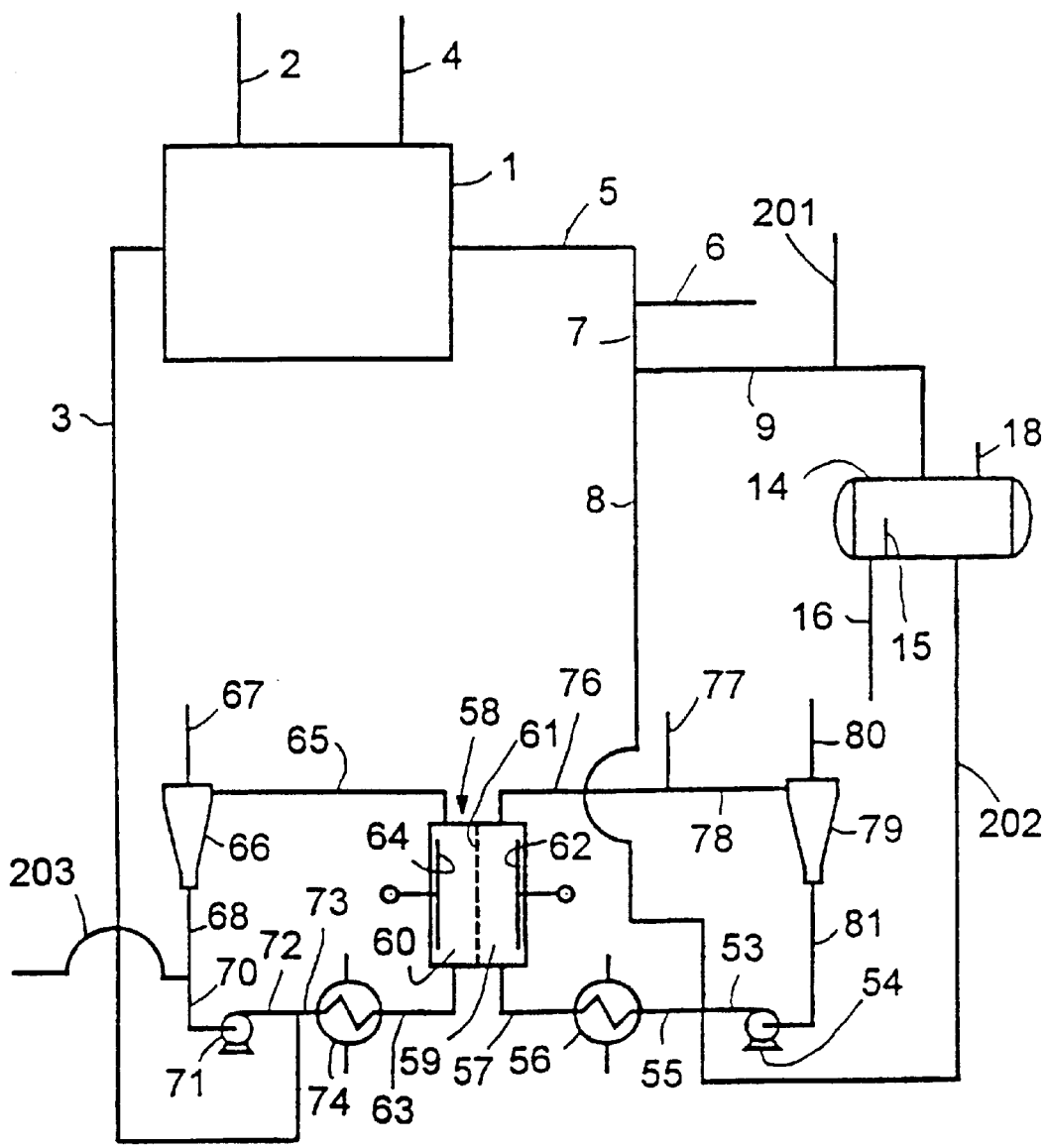
FIG. 3 is a flow diagram of another form of plant for treatment of an alkaline aqueous waste stream.

FIG. 3 shows another form of plant constructed in accordance with the invention. Plant 1 is in this case, a plant for production of neopentyl glycol by reaction of iso-butyraldehyde with formaldehyde. As in the case, of FIG. 2, like reference numerals refer to like items in FIG. 3 to those used in FIG. 1. The aqueous alkaline waste liquor in line 5 contains sodium iso-butyrate and sodium hydroxypivalate. Iso-butanol is added in line 201; whilst this solvent is partially soluble in water, the presence of inorganic salts in the aqueous phase in line 9 (for example, sodium sulphate if the acid recycled in line 8 comprises sulphuric acid) reduces its solubility in the aqueous phase. However, water dissolves in the iso-butanol layer as well as the carboxylic acids (iso-butyric acid and hydroxypivalic acid). In decanter 14, the organic acid layer overflowing weir 15 to line 16 thus comprises iso-butanol, carboxylic acids (iso-butyric acid and hydroxypivalic acid), and water. The resulting stream in line 16 can be separated by any suitable method, e.g. by distillation and the iso-butanol recovered for recycle to line 201.

The resulting acidic predominantly aqueous liquor passes on in line 202 from decanter 14 for admixture with the recirculating stream in line 53. In electrolysis zone 58 one mole of water is generated for every two moles of sodium hydroxide that is generated in cathode compartment 60. By appropriate choice of the rate of supply of iso-butanol in line 201 it is possible to remove in the stream in line 16 the net amount of water present in the waste liquor in line 5 (i.e. the total amount of water present in the waste liquor in line 5 less the quantity of water consumed in electrolysis zone 58). In addition, water is supplied in line 203 in sufficient amount to provide in the sodium hydroxide solution in line 3 the water required to maintain the water balance in plant 1.

Whilst the plant 1 of FIG. 3 is described as a neopentyl production facility, it will be appreciated by those skilled in the art that plant 1 could alternatively be an aldolisation plant used, for example, for the production of 2-ethylhex-2-enal from n-butyraldehyde.

The invention is further illustrated in the following Examples.

EXAMPLE 1

An experimental rig having the general layout of part of the plant of FIG. 1 was used to treat an aqueous solution obtained From an aldolisation plant making 2-ethylhex-2-enal from n-butyraldehyde. A solution containing 9.5% w/w of sodium n-butyrate and 0.6% w/w sodium hydroxide as well as other minor impurities was supplied in line 5 at a rate of 537 g/hr. This solution was combined with material from line 8 at a rate of 536 g/hr. At start up of the rig dilute phosphoric acid (12% w/w) was supplied in line 6 until the process system was full including some buffer tanks (not shown).

The mixed solution was sent via lines 9, 10 and 11 to distillation column 12; valves (not shown) were used to close lines 13 and 17. The distillation column 12 was operated such that the composition exiting the bottom of the column 12 in line 48 was essentially free from n-butyric acid. This bottoms stream was used as feed in line 52 for electrolysis zone 58.

The overhead stream from distillation column 12 was collected in a buffer tank (not shown) and used as feed in line 32 for the second distillation column 33. The feed rate to the second distillation column 33 was 484 g/hr. The second distillation column 33 was operated in such a way that the overhead mixture in line 35 was essentially that of the water-n-butyric acid azeotrope, together with some minor impurities leaving the rig in line 42.

The bottoms product from distillation column 33 was essentially free from n-butyric acid and other impurities and was used as make up water in line 47 for cathode compartment 60. (Cathode compartment 60 had been charged with dilute (5% w/w) sodium hydroxide during start up of the electrolysis zone 58).

The bottoms product from distillation column 12 was passed in line 52 to a buffer tank (not shown) and from thence to the anode compartment 59.

The anode compartment contained an iridium oxide coated titanium anode plate 62. The membrane 61 was a NAFION™ cation exchanger membrane. The cathode compartment contained a stainless steel cathode plate 64. The area of each major face of each electrode was 0.01 m². The recirculation rate through the anode compartment and through the cathode compartment was in each case 200 l/hr; these recycle flow rates were monitored by means of flowmeters (not shown).

The temperature in electrolysis zone was maintained between 45° C. and 50° C. by adjustment of the cooling water flow rates through heat exchangers 56 and 74. For steady state operation of the rig the buffer tanks (not shown) were equipped with level controllers in order to ensure a constant inventory within the rig.

During steady state operation the cell current was 20 amperes and the voltage was 5.8 v.

The results obtained are summarised in Table 1 below.

TABLE 1

| Line No. | 5 | 8 | 9 | 52 | 3 | 32 | 42 | 47 |
|---|---|---|---|---|---|---|---|---|
| Units | % w/w | % w/w | % w/w | % w/w | % w/w | % w/w | % w/w | % w/w |
| NaOH | 0.6 | 0.0 | 0.0 | 0.0 | 7.0 | 0.0 | 0.0 | 0.0 |
| CH₃CH₂CH₂COONa | 9.5 | 0.0 | 0.0 | 0.0 | 0.0 | 0.0 | 0.0 | 0.0 |
| NaH₂PO₄ | 0.0 | 19.4 | 15.8 | 28.3 | 0.0 | 0.0 | 0.0 | 0.0 |

TABLE 1-continued

| Line No. | 5 | 8 | 9 | 52 | 3 | 32 | 42 | 47 |
|---|---|---|---|---|---|---|---|---|
| Units | % w/w | % w/w | % w/w | % w/w | % w/w | % w/w | % w/w | % w/w |
| $H_3PO_4$ | 0.0 | 11.4 | 1.0 | 1.8 | 0.0 | 0.0 | 0.0 | 0.0 |
| $CH_3CH_2CH_2COOH$ | 0.0 | 0.0 | 3.7 | 0.0 | 0.0 | 8.5 | 18.4 | 0.0 |
| Organic impurities | trace | trace | trace | trace | | trace | trace | trace |
| $H_2O$ | 89.9 | 69.2 | 79.4 | 69.9 | 93.0 | 91.5 | 81.6 | 100.0 |
| Flowrate (g/hr) | 537 | 563 | 1099 | 616 | 310 | 48 | 222 | 262 |

EXAMPLE 2

The rig of Example 1 was operated with the same feed and under essentially the same conditions as in Example 1 except that dilute (10% w/w) sulphuric acid was used in place of phosphoric acid. The results set out in Table 2 were obtained.

TABLE 2

| Units | 5 % w/w | 8 % w/w | 9 % w/w | 52 % w/w | 3 % w/w | 32 % w/w | 42 % w/w | 47 % w/w |
|---|---|---|---|---|---|---|---|---|
| NaOH | 0.5 | 0.0 | 0.0 | 0.0 | 6.8 | 0.0 | 0.0 | 0.0 |
| $CH_3CH_2CH_2COONa$ | 9.5 | 0.0 | 0.0 | 0.0 | 0.0 | 0.0 | 0.0 | 0.0 |
| $Na_2SO_4$ | 0.0 | 5.9 | 6.4 | 11.5 | 0.0 | 0.0 | 0.0 | 0.0 |
| $H_2SO_4$ | 0.0 | 4.6 | 0.1 | 0.1 | 0.0 | 0.0 | 0.0 | 0.0 |
| $CH_3CH_2CH_2COOH$ | 0.0 | 0.0 | 3.7 | 0.0 | 0.0 | 8.4 | 18.4 | 0.0 |
| Organic impurities | trace | trace | trace | trace | | trace | trace | trace |
| $H_2O$ | 90.0 | 89.4 | 89.8 | 88.4 | 93.2 | 91.6 | 81.6 | 100.0 |
| Flowrate (g/hr) | 405 | 432 | 838 | 470 | 235 | 368 | 167 | 200 |

EXAMPLE 3

The experimental rig of Examples 1 and 2 was modified so as to correspond to part of the flow sheet of FIG. 2 and was used for the treatment of an aqueous alkaline liquor from a plant for producing neo-pentyl glycol from iso-butyraldehyde and formaldehyde was investigated.

A solution containing 15.1% w/w sodium iso-butyrate, 14.1% w/w sodium hydroxypivalate, and 0.6% w/w sodium hydroxide, as well as other minor impurities, was supplied in line 5 at a rate of 242 g/hr. This solution was combined with material from line 8 which was supplied at a rate of 639 g/hr. During start up of the rig dilute (10% w/w) sulphuric acid was supplied in line 6 until the buffer tanks (not shown) and the rest of the system were full. Distillation column 12 was operated in such a manner that the composition exiting the bottom of the column in line 48 was essentially free of iso-butyric acid and surplus water; in addition, this bottoms stream contained some hydroxypivalic acid. However, due to the low pH of the solution in the anode compartment 59, the presence of the hydroxypivalic acid proved not to have any deleterious effect upon the smooth operation of the electrolysis zone 58. The overhead product from distillation column 12 was collected after condensation in decanter 25, having been mixed with the overhead product from the second distillation column 33. The lower aqueous phase from decanter 25 is used as feed for the second distillation column 33, the upper organic phase being recycled to the decanter 14 in line 101. Second distillation column 33 was operated in such a way as to produce an overhead product whose composition was essentially that of the iso-butyric acid/water azeotrope, plus some minor impurities. The bottoms product from second distillation column 33 was essentially free from iso-butyric acid and other impurities and was passed in line 47 to cathode compartment 60, after mixing with any necessary sodium hydroxide and deionised water supplied in line 75. Cathode compartment 60 had been charged with dilute (5% w/w) sodium hydroxide at start up of the rig. The bottoms product from distillation column 12 was pumped via a buffer tank (not shown) to the anode compartment 59

The current between the iridium oxide coated titanium anode 62 and the stainless steel cathode 64 was 20 amperes, the voltage being 5.6 volts d.c.

The results set out in Table 3 were obtained.

TABLE 3

| Line No. | 5 | 52 | 8 | 102 | 101 | 16 | 104 | 47 | 3 | 75 |
|---|---|---|---|---|---|---|---|---|---|---|
| Units | % w/w | % w/w | % w/w | % w/w | % w/w | % w/w | % w/w | % w/w | % w/w | % w/w |
| NaOH | 0.1 | 0.0 | 0.0 | 0.0 | 0.0 | 0.0 | 0.0 | 0.0 | 12.0 | 0.0 |
| $(CH_3)_2CHCOONa$ | 15.1 | 0.0 | 0.0 | 0.0 | 0.0 | 0.0 | 0.0 | 0.0 | 0.0 | 0.0 |
| $(CH_3)_2C(CH_2OH)COONa$ | 14.1 | 0.0 | 0.0 | 0.0 | 0.0 | 0.0 | 0.0 | 0.0 | 0.0 | 0.0 |
| $Na_2SO_4$ | 0.0 | 20.0 | 15.5 | 16.0 | 0.0 | 2.5 | 17.0 | 0.0 | 0.0 | 0.0 |
| $H_2SO_4$ | 0.0 | 0.2 | 4.7 | 0.1 | 0.0 | 0.0 | 0.1 | 0.0 | 0.0 | 0.0 |
| $(CH_3)_2CHCOOH$ | 0.0 | 0.0 | 0.0 | 3.3 | 68.7 | 28.3 | 3.1 | 0.0 | 0.0 | 0.0 |
| $(CH_3)_2C(CH_2OH)COOH$ | 0.0 | 4.6 | 5.0 | 6.9 | 0.0 | 27.8 | 3.9 | 0.0 | 0.0 | 0.0 |
| $H_2O$ | 70.7 | 75.2 | 74.8 | 73.7 | 31.3 | 41.5 | 75.9 | 100.0 | 88.0 | 100.0 |
| Flow rate (g/hr) | 242 | 689 | 639 | 881 | 37 | 104 | 814 | 88 | 182 | 45 |

What is claimed is:

1. A process for treating an aqueous waste stream from a chemical production plant, which aqueous waste stream contains at least one alkali metal carboxylate containing at least 3 carbon atoms, to produce a solution of an alkali metal hydroxide for recycle to the chemical production plant, which process comprises:
   (a) admixing the waste stream with a dilute aqueous solution of an inorganic acid selected from phosphoric acid, sulphuric acid, or a mixture thereof so as to generate from said at least one alkali metal carboxylate a corresponding carboxylic acid or acids and to produce an acidic liquor having a pH of less than about 3.5 and containing an alkali metal salt of the inorganic acid;
   (b) separating free carboxylic acid or acids from the acidic liquor of step (a) to form an acidic predominantly aqueous phase containing the alkali metal salt of the inorganic acid;
   (c) providing an electrolysis zone comprising an anode compartment and a cathode compartment, the anode compartment containing an anode and the cathode compartment containing a cathode, and the anode compartment being separated from the cathode compartment by means of an ion permeable membrane permeable to alkali metal ions;
   (d) supplying the acidic predominantly aqueous phase resulting from step (b) to the anode compartment of the electrolysis zone;
   (e) supplying water to the cathode compartment of the electrolysis zone;
   (f) passing a current between the anode and the cathode thereby to subject the acidic predominantly aqueous phase to electrolysis, to cause alkali metal ions to pass through the ion permeable membrane from the anode compartment to the cathode compartment and form alkali metal hydroxide therein, and to regenerate inorganic acid in the anode compartment;
   (g) recovering from the cathode compartment an alkali metal hydroxide solution for recycle to the chemical production plant; and
   (h) recycling a solution containing the inorganic acid produced in step (f) to step (a).

2. A process according to claim 1, wherein the chemical production plant is an aldolisation plant in which a saturated aliphatic aldehyde containing at least 3 carbon atoms is subjected to aldolisation and dehydration in the presence of an alkali catalyst selected from an alkali metal hydroxide and an alkali metal carbonate to form an unsaturated aldehyde containing twice as many carbon atoms as the saturated aliphatic aldehyde.

3. A process according to claim 2, in which the saturated aliphatic aldehyde is n-butyraldehyde.

4. A process according to claim 1, in which the chemical production plant is a plant for converting iso-butyraldehyde to neopentyl glycol by reaction with formaldehyde in the presence of an alkali catalyst selected from an alkali metal hydroxide and an alkali metal carbonate.

5. A process according to claim 1, in which step (b) includes subjecting the acidic liquor to distillation in a first distillation zone maintained under distillation conditions effective for distillation of free carboxylic acid and water from the acidic liquor to form the acidic predominantly aqueous phase.

6. A process according to claim 5, in which there is recovered from the first distillation zone an overhead product comprising the carboxylic acid or acids and water, as well as minor organic by-products, and in which the overhead product is condensed and allowed to separate to form an organic layer which is purged and an aqueous liquid containing free carboxylic acid or acids.

7. A process according to claim 6, in which at least a part of the aqueous liquid is subjected to a second distillation step in a second distillation zone maintained under distillation conditions effective for distillation of a mixture of water and free carboxylic acid from a bottoms stream comprising substantially pure water.

8. A process according to claim 7, in which the bottoms stream from the second distillation zone is passed to the cathode compartment.

9. A process according to claim 8, in which the bottoms stream is admixed with liquor recycled from the cathode compartment to form a mixed feed stream for admission to the cathode compartment.

10. A process according to claim 9, in which the mixed feed stream is pumped through the cathode compartment at a rate sufficient to sweep at least a majority of the gas bubbles generated by electrolysis off the surface of the cathode substantially as fast as they are formed.

11. A process according to claim 5, in which the acidic predominantly aqueous phase is admixed with liquor recycled from the anode compartment to form a mixed acidic liquor for admission to the anode compartment.

12. A process according to claim 11, in which the mixed acidic liquor is pumped through the anode compartment at a rate sufficient to sweep at least a majority of the gas bubbles generated by electrolysis off the surface of the anode substantially as fast as they are formed.

13. A process according to claim 1, in which step (b) includes passing the acidic liquor to a settling zone, recovering from the settling zone an organic phase comprising free carboxylic acid and an aqueous phase, and subjecting the aqueous phase to distillation in a first distillation zone maintained under distillation conditions effective for distillation of free carboxylic acid and water from the acidic liquor to form the acidic predominantly aqueous phase.

14. A process according to claim 13, in which a substantially water-insoluble solvent is mixed with the acidic liquor prior to passage to the settling zone.

15. A process according to claim 13, in which there is recovered from the first distillation zone an overhead product comprising the carboxylic acid or acids and water, and in which the overhead product is condensed and allowed to separate to form an organic layer comprising free carboxylic acid or acids which is recycled to the settling zone and an aqueous liquid.

16. A waste treatment plant for treating an aqueous waste stream from a chemical production plant, which aqueous waste stream contains at least one alkali metal carboxylate containing at least 3 carbon atoms, to produce a solution of an alkali metal hydroxide for recycle to the chemical production plant, the waste treatment plant comprising:
   (a) means for admixing the waste stream with a dilute aqueous solution of an inorganic acid selected from phosphoric acid, sulphuric acid, or a mixture thereof so as to generate from said at least one alkali metal carboxylate a corresponding carboxylic acid or acids and to produce an acidic liquor having a pH of less than about 3.5 and containing an alkali metal salt of the inorganic acid;
   (b) means for separating free carboxylic acid or acids from the acidic liquor of step (a) to form an acidic predominantly aqueous phase containing the alkali metal salt of the inorganic acid;

(c) an electrolysis zone comprising an anode compartment and a cathode compartment, the anode compartment containing an anode and the cathode compartment containing a cathode, and the anode compartment being separated from the cathode compartment by means of an ion permeable membrane permeable to alkali metal ions;

(d) means for supplying the acidic predominantly aqueous chase to the anode compartment of the electrolysis zone;

(e) means for supplying water to the cathode compartment of the electrolysis zone;

(f) means for passing a current between the anode and the cathode thereby to subject the acidic predominantly aqueous phase to electrolysis, to cause alkali metal ions to pass through the ion permeable membrane from the anode compartment to the cathode compartment and form alkali metal hydroxide therein, and to regenerate inorganic acid in the anode compartment;

(g) means for recovering from the cathode compartment an alkali metal hydroxide solution for recycle to the chemical production plant;

(h) means for recycling a solution containing the inorganic acid produced in the anode compartment to the admixing means (a); and (i) means for recovering the liquid stream of free carboxylic acid or acids separated in the separating means (b).

17. A waste treatment plant according to claim 16, wherein the chemical production plant is an aldolisation plant in which a saturated aliphatic aldehyde containing at least 3 carbon atoms is subjected to aldolisation and dehydration in the presence of an alkali catalyst selected from an alkali metal hydroxide and an alkali metal carbonate to form an unsaturated aldehyde containing twice as many carbon atoms as the saturated aliphatic aldehyde.

18. A waste treatment plant according to claim 17, in which the chemical production plant is an aldolisation plant for conversion of n-butyraldehyde to 2-ethylhex-2-enal.

19. A waste treatment plant according to claim 16, in which the chemical production plant is a plant for converting iso-butyraldehyde to neopentyl glycol by reaction with formaldehyde in the presence of an alkali catalyst selected from an alkali metal hydroxide and an alkali metal carbonate.

20. A waste treatment plant according to claim 16, in which the means for separating free carboxylic acid or acids from the acidic liquor of step (a) to form an acidic predominantly aqueous phase containing the alkali metal salt of the inorganic acid comprises a first distillation zone maintained under distillation conditions effective for distillation of free carboxylic acid and water from the acidic liquor to form the acidic predominantly aqueous phase.

21. A waste treatment plant according to claim 20, which includes a second distillation zone maintained under distillation conditions effective for distillation from the aqueous liquid recovered from the first distillation step of a mixture of water and free carboxylic acid and to form a bottoms stream comprising substantially pure water.

22. A waste treatment plant according to claim 21, in which the means for supplying water to the cathode compartment of the electrolysis zone comprises means for passing the bottoms stream from the second distillation zone to the cathode compartment.

23. A waste treatment plant according to claim 22, further including means for admixing the bottoms stream with liquor recycled from the cathode compartment to form a mixed feed stream for admission to the cathode compartment.

24. A waste treatment plant according to claim 23, in which the means for passing the bottoms stream from the second distillation zone to the cathode compartment includes a pump adapted to pump the mixed feed stream through the cathode compartment at a rate sufficient to sweep at least a majority of the gas bubbles generated by electrolysis off the surface of the cathode substantially as fast as they are formed.

25. A waste treatment plant according to any one of claim 16, in which the means for separating free carboxylic acid or acids from the acidic liquor of step (a) to form an acidic predominantly aqueous phase containing the alkali metal salt of the inorganic acid comprises a settling zone, means for recovering from the settling zone an upper organic phase comprising free carboxylic acid and a lower aqueous phase, and a first distillation zone maintained under distillation conditions effective for distillation of free carboxylic acid and water from the lower aqueous phase.

26. A waste treatment plant according to any one of claim 16, in which the means for supplying the acidic predominantly aqueous phase to the anode compartment of the electrolysis zone comprises means for admixing the acidic predominantly aqueous phase with liquor recycled from the anode compartment to form a mixed acidic liquor for admission to the anode compartment.

27. A waste treatment plant according to claim 26, in which the means for supplying the acidic predominantly aqueous phase to the anode compartment of the electrolysis zone further includes a pump for pumping mixed acidic liquor through the anode compartment at a rate sufficient to sweep at least a majority of the gas bubbles generated by electrolysis off the surface of the anode substantially as fast as they are formed.

* * * * *